United States Patent
Kato et al.

[11] Patent Number: 5,942,190
[45] Date of Patent: *Aug. 24, 1999

[54] OXIDE SENSOR

[75] Inventors: Nobuhide Kato, Ama-gun; Kunihiko Nakagaki, Nagoya, both of Japan

[73] Assignee: NGK Insulators, Ltd., Japan

[*] Notice: This patent is subject to a terminal disclaimer.

[21] Appl. No.: 08/802,280

[22] Filed: Feb. 19, 1997

[30] Foreign Application Priority Data

Feb. 23, 1996 [JP] Japan .................................. 8-036422
Feb. 7, 1997 [JP] Japan .................................. 9-025573

[51] Int. Cl.$^6$ .................................................. G01N 27/41
[52] U.S. Cl. ............................. 422/98; 422/83; 436/116; 436/118; 73/31.05; 204/425; 204/426; 204/427
[58] Field of Search .................... 422/83, 90, 98; 436/116, 117, 118; 73/31.05; 204/425, 426, 427, 406

[56] References Cited

U.S. PATENT DOCUMENTS

| | | | |
|---|---|---|---|
| 4,859,307 | 8/1989 | Nishizawa et al. | 204/425 |
| 4,927,517 | 5/1990 | Mizutani et al. | 204/406 |
| 5,034,112 | 7/1991 | Murase et al. | 204/406 |
| 5,049,254 | 9/1991 | Logothetis et al. | 204/425 |
| 5,145,566 | 9/1992 | Logothetis et al. | 204/153.18 |
| 5,217,588 | 6/1993 | Wang et al. | 204/153.1 |
| 5,298,147 | 3/1994 | Nakae et al. | 204/424 |
| 5,302,275 | 4/1994 | Dietz et al. | 204/424 |
| 5,413,683 | 5/1995 | Murase et al. | 204/183.16 |
| 5,630,920 | 5/1997 | Friese et al. | 204/424 |
| 5,672,811 | 9/1997 | Kato et al. | 73/31.05 |
| 5,676,811 | 10/1997 | Makino et al. | 204/425 |
| 5,709,787 | 1/1998 | Lim | 204/425 |

FOREIGN PATENT DOCUMENTS

| | | |
|---|---|---|
| 0 188 900 A2 | 7/1986 | European Pat. Off. . |
| 0 257 842 A2 | 3/1988 | European Pat. Off. . |
| 0 257 842 A3 | 3/1988 | European Pat. Off. . |
| 0 678 740 A1 | 10/1995 | European Pat. Off. . |
| 0 731 351 A2 | 9/1996 | European Pat. Off. . |
| 0 731 351 A3 | 9/1996 | European Pat. Off. . |
| 44 39 901 A1 | 5/1996 | Germany . |
| 2 288 873 | 11/1995 | United Kingdom . |
| WO 95/30146 | 11/1995 | WIPO . |

*Primary Examiner*—Long V. Le
*Attorney, Agent, or Firm*—Parkhurst & Wendel, L.L.P.

[57] ABSTRACT

Disclosed is an oxide sensor in which a measuring electrode is arranged at a distance d to satisfy $-3t \leq d \leq 3t$ for a downstream end of an inner pumping electrode for a first chamber, i.e., the end located on a side of a second diffusion rate-determining section, provided that d represents a distance between the measuring electrode and the downstream end in a positive direction directed from the first chamber to a second chamber, and t represents a height of the first chamber. A partial pressure of oxygen in the first chamber is measured by using the measuring electrode. A main pumping cell is subjected to feedback control on the basis of a measured value so that the partial pressure of oxygen in the first chamber is controlled. After that, a measurement gas is introduced into the second chamber. Oxides contained in the measurement gas are decomposed by the aid of a detecting electrode or a catalyst. A partial pressure of oxygen produced by the decomposition is measured to determine the concentration of the oxides. Accordingly, it is possible to measure the oxides contained in the measurement gas with an extremely high degree of accuracy. Moreover, the obtainable oxide sensor is compact and inexpensive.

21 Claims, 9 Drawing Sheets

OXIDE SENSOR

BACKGROUND OF THE INVENTION

1. Field of the Invention

The present invention relates to an oxide sensor for measuring oxides contained in, for example, atmospheric air and exhaust gas discharged from vehicles or automobiles, such as NO, $NO_2$, $SO_2$, $CO_2$, and $H_2O$. In particular, the present invention relates to an oxide sensor for measuring NO and $NO_2$.

2. Description of the Related Art

Exhaust gas, which is discharged, for example, from vehicles or automobiles such as gasoline-fueled automobiles and diesel powered automobiles, contains nitrogen oxides (NOx) such as nitrogen monoxide (NO) and nitrogen dioxide ($NO_2$), as well as carbon monoxide (CO), carbon dioxide ($CO_2$), water ($H_2O$), hydrocarbon (HC), hydrogen ($H_2$), oxygen ($O_2$) and so on. In such exhaust gas, about 80% of the entire NOx is occupied by NO, and about 95% of the entire NOx is occupied by NO and $NO_2$.

The three way catalyst, which is used to clean HC, CO, and NOx contained in the exhaust gas, exhibits its maximum cleaning efficiency in the vicinity of the theoretical air fuel ratio (A/F=14.6). If A/F is controlled to be not less than 16, the amount of produced NOx is decreased. However, the cleaning efficiency of the catalyst is lowered, and consequently the amount of discharged NOx is apt to increase.

Recently, in order to effectively utilize fossil fuel and avoid global warming, the market demand increases, for example, in that the discharge amount of $CO_2$ should be suppressed. In order to respond to such a demand, it becomes more necessary to improve the fuel efficiency. In response to such a demand, for example, the lean burn engine and the catalyst for cleaning NOx are being researched. Especially, the need for a NOx sensor increases.

A conventional NOx analyzer has been hitherto known as an instrument for detecting NOx. The conventional NOx analyzer is operated to measure a characteristic inherent in NOx, based on the use of chemical luminous analysis. However, the conventional NOx analyzer is inconvenient in that the instrument itself is extremely large and expensive. The conventional NOx analyzer requires frequent maintenance because optical parts are used to detect NOx. Further, when the conventional NOx analyzer is used, any sampling operation should be performed for measurement of NOx, where it is impossible to directly insert a detecting element itself into a fluid. Therefore, the conventional NOx analyzer is not suitable for analyzing transient phenomena such as those occur in the exhaust gas discharged from an automobile, in which the condition frequently varies.

In order to dissolve the inconveniences as described above, there has been already suggested a sensor for measuring a desired gas component in exhaust gas by using a substrate comprising an oxygen ion-conductive solid electrolyte.

FIG. 11 shows a system of a gas analyzer disclosed in International Publication WO 95/30146. This apparatus comprises a first chamber 4 into which a measurement gas containing NO is introduced through a narrow hole 2, and a second chamber 8 into which the measurement gas is introduced from the first chamber 4 through a narrow hole 6. Wall surfaces for constructing the first and second chambers 4, 8 are composed of partition walls 10a, 10b made of zirconia ($ZrO_2$) capable of transmitting oxygen ion. A pair of measuring electrodes 12a, 12b and a pair of measuring electrodes 14a, 14b for measuring the partial pressure of oxygen in the respective chambers are arranged on portions of one $ZrO_2$ partition wall 10a corresponding to the first and second chambers 4, 8 respectively. A set of pumping electrodes 16a, 16b and a set of pumping electrodes 18a, 18b for pumping out $O_2$ in the respective chambers to the outside of the chambers are arranged on the other $ZrO_2$ partition wall 10b.

The gas analyzer thus constructed functions as follows. Namely, the partial pressure of oxygen contained in the measurement gas introduced into the first chamber 4 through the narrow hole 2 is detected by a voltmeter 20 as an electric potential difference generated between the measuring electrodes 12a, 12b. A voltage of 100 to 200 mV is applied between the pumping electrodes 16a, 16b by the aid of a power source 22 so that the electric potential difference is adjusted to have a predetermined value. Accordingly, $O_2$ in the first chamber 4 is pumped out to the outside of the apparatus. The amount of pumped out oxygen can be measured by using an ammeter 24.

The measurement gas, from which almost all $O_2$ has been removed, is introduced into the second chamber 8 through the narrow hole 6. In the second chamber 8, an electric potential difference generated between the measuring electrodes 14a, 14b is detected by a voltmeter 26. Thus the partial pressure of oxygen in the second chamber 8 is measured. On the other hand, NO contained in the measurement gas introduced into the second chamber 8 is decomposed as follows by the aid of a voltage applied between the pumping electrodes 18a, 18b by means of a power source 28:

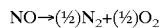

$O_2$ produced by the decomposition is pumped out to the outside of the second chamber 8 by the aid of the pumping electrodes 18a, 18b. A value of an electric current generated during this process is detected by an ammeter 30. Thus the concentration of NO contained in the measurement gas is measured.

However, the gas analyzer constructed as described above causes the following inconvenient situation. Namely, when the concentration of $O_2$ contained in the measurement gas is high, a high voltage is applied between the pumping electrodes 16a, 16b on the basis of an electric potential difference measured by the voltmeter 20, in order to remove $O_2$. In this process, $O_2$ in the first chamber 4 is excessively eliminated. As a result, an equilibrium state established between NO and other gases in the first chamber 4 collapses, resulting in a situation in which NO is decomposed on the pumping electrode 16b. When such a situation occurs, it is impossible to accurately measure the concentration of NO, based on the measurement gas introduced into the second chamber 8. When the concentration of $O_2$ is low, the decomposition of NO may scarcely occur, because the voltage applied between the pumping electrodes 16a, 16b is low.

SUMMARY OF THE INVENTION

The present invention has been made in order to overcome the inconvenience described above, an object of which is to provide an oxide sensor which makes it possible to measure oxides contained in a measurement gas with an extremely high degree of accuracy, the oxide sensor being compact and inexpensive.

In order to achieve the object described above, the present invention provides an oxide sensor comprising a main pumping means including a solid electrolyte for contacting with external space, and inner and outer electrodes formed on inner and outer surfaces of the solid electrolyte, for performing a pumping process for oxygen contained in a measurement gas introduced from the external space, on the basis of a control voltage applied between the electrodes; a concentration-measuring means including a solid electrolyte, an inner measuring electrode formed on the solid electrolyte so that the inner measuring electrode is opposed to the inner pumping electrode of the main pumping means, and an outer measuring electrode formed on the solid electrolyte on a side-opposite to the inner measuring electrode, for measuring an electromotive force of an oxygen concentration cell, generated corresponding to a difference in partial pressure between oxygen resulting from the pumping process performed by the main pumping means and oxygen contained in a gas existing on a side of the outer measuring electrode; a main pumping control means for adjusting a level of the control voltage so that the electromotive force of the oxygen concentration cell detected by the concentration-measuring means has a predetermined value; and an electric signal-generating conversion means including a solid electrolyte and inner and outer detecting electrodes provided in contact with the solid electrolyte, for providing, by conversion, an electric signal corresponding to an amount of oxygen contained in the measurement gas after being subjected to the pumping process performed by the main pumping means; wherein the inner measuring electrode is arranged at a position at which $-3t \leq d$ is satisfied provided that a downstream direction along a space for the pumping process performed by the main pumping means is defined as a positive direction, a height of the space for the pumping process is represented by t, and a projective distance between a downstream end of the inner pumping electrode of the main pumping means and a center of the inner measuring electrode of the concentration-measuring means is represented by d, and wherein oxides in the measurement gas are measured on the basis of the electric signal supplied from the electric signal-generating conversion means.

According to the present invention, at first, the oxygen in the measurement gas introduced from the external space is subjected to the pumping process performed by the main pumping means, and the oxygen is adjusted to have a predetermined concentration. The measurement gas, in which the oxygen concentration has been adjusted by the main pumping means, is introduced into the electric signal-generating conversion means in the next step. The electric signal-generating conversion means performs conversion into the electric signal corresponding to an amount of oxygen contained in the measurement gas after being subjected to the pumping process performed by the main pumping means. After that, the oxides contained in the measurement gas are measured on the basis of the electric signal supplied from the electric signal-generating conversion means.

During the operation described above, the electromotive force is generated corresponding to a difference between an amount of oxygen contained in the measurement gas upon the pumping process performed by the main pumping means and an amount of oxygen contained in the gas existing on the side of the outer measuring electrode. The level of the control voltage applied between the inner and outer pumping electrodes of the main pumping means is adjusted on the basis of the electromotive force by the aid of the main pumping control means.

The main pumping means performs the pumping process for an amount of the oxygen in the measurement gas introduced from the external space, the amount corresponding to the level of the control voltage. The oxygen concentration in the measurement gas is subjected to feedback control so that the oxygen concentration is at a predetermined level, by supplying, to the main pumping means, the control voltage having been subjected to the adjustment for the level as described above.

According to the present invention, the inner measuring electrode is arranged at a position at which $-3t \leq d$ is satisfied, preferably $-3t \leq d \leq 3t$ is satisfied provided that the downstream direction along the space for the pumping process performed by the main pumping means is defined as the positive direction, the height of the space for the pumping process is represented by t, and the projective distance between the downstream end of the inner pumping electrode of the main pumping means and the center of the inner measuring electrode of the concentration-measuring means is represented by d. Thus the partial pressure of oxygen after being subjected to the pumping process performed by the main pumping means can be measured highly accurately, making it possible to improve the accuracy of the adjustment of the control voltage for the main pumping means performed by the main pumping control means, and improve the reliability. As a result, the pumping process for oxygen is performed, while favorably suppressing the decomposition of the oxides on the inner pumping electrode of the main pumping means.

The oxide sensor may further comprise a measuring pumping means and a current-detecting means to serve as the electric signal-generating conversion means. In this preferred embodiment, the measurement gas, in which the oxygen concentration has been adjusted by the main pumping means, is introduced into the measuring pumping means. The oxygen in the measurement gas is subjected to a pumping process by the aid of the measuring pumping means on the basis of a measuring voltage applied between inner and outer detecting electrodes. A pumping current is generated in the measuring pumping means, corresponding to an amount of oxygen subjected to the pumping process performed by the measuring pumping means. The generated pumping current is detected by the current-detecting means. Thus the oxides are measured, corresponding to the amount of oxygen.

As for the measuring pumping means, a pumping voltage sufficient to decompose the oxides is applied between the inner and outer detecting electrodes, and/or the measuring pumping means is arranged with an oxide-decomposing catalyst for decomposing the oxides. In such an embodiment, oxygen is produced from the oxides decomposed by the action of the pumping voltage and/or the action of the oxide-decomposing catalyst. The produced oxygen is subjected to the pumping process, and the pumping current thereby generated is detected by the current-detecting means. Thus the oxides are measured, corresponding to the amount of oxygen.

In another preferred embodiment, the oxide sensor of the present invention may further comprise a concentration-detecting means and a voltage-detecting means to serve as the electric signal-generating conversion means. In this embodiment, the measurement gas, in which the concentration of oxygen has been adjusted by the main pumping means, is introduced into the concentration-detecting means in the next step. The concentration-detecting means generates an electromotive force of an oxygen concentration cell, corresponding to a difference between an amount of oxygen contained in the measurement gas after being subjected to the pumping process performed by the main pumping means and an amount of oxygen contained in the gas existing on the side of the outer detecting electrode. The generated electromotive force is detected by the voltage-detecting means. Thus the oxides are measured, corresponding to the amount of oxygen.

In still another preferred embodiment concerning the concentration-detecting means, the concentration-detecting means is arranged with an oxide-decomposing catalyst for decomposing the oxides. Accordingly, an electromotive force of an oxygen concentration cell is generated between the inner and outer detecting electrodes, corresponding to a difference between an amount of oxygen produced from the oxides decomposed by the action of the oxide-decomposing catalyst and an amount of oxygen contained in the gas existing on the side of the outer detecting electrode. The generated electromotive force is detected by the voltage-detecting means. Thus the oxides are measured, corresponding to the amount of oxygen.

In the oxide sensor constructed as described above, it is preferable that a width w of the inner measuring electrode of the concentration-measuring means along the downstream direction satisfies w≦5t. Thus it is possible to suppress decomposition of the oxides on the inner measuring electrode.

In the oxide sensor constructed as described above, it is preferable that the inner pumping electrode of the main pumping means is composed of an inactive material having a low catalytic activity on the oxides. In this embodiment, the decomposing action on the oxides on the inner pumping electrode is suppressed more appropriately. Especially, it is possible to highly accurately measure nitrogen oxide including NO or $NO_2$.

The oxide sensor constructed as described above may further comprise an auxiliary pumping means including an auxiliary pumping electrode formed in the vicinity of the inner detecting electrode, wherein the oxygen contained in the measurement gas after being subjected to the pumping process performed by the main pumping means is subjected to a pumping process on the basis of a voltage applied between the auxiliary pumping electrode and the outer detecting electrode.

Accordingly, the measurement gas, which has been firstly subjected to the coarse adjustment so that the predetermined gas component has a predetermined concentration by the aid of the main pumping means, is further subjected to the fine adjustment for the concentration of the predetermined gas component by the aid of the auxiliary pumping means.

In general, when the concentration of the predetermined gas component in the measurement gas in the external space greatly changes (for example, from 0 to 20%), the concentration distribution of the predetermined gas component in the measurement gas introduced into the main pumping means greatly changes. The amount of the predetermined gas component introduced into the measuring pumping means or the concentration-detecting means also changes.

In such a situation, the oxygen concentration in the measurement gas after being subjected to the pumping process performed by the main pumping means is finely adjusted upon the pumping process performed by the auxiliary pumping means. Significantly, the change in oxygen concentration in the measurement gas introduced into the auxiliary pumping means is greatly reduced as a result of the pumping process performed by the main pumping means, as compared with the change in oxygen concentration in the measurement gas supplied from the external space (the measurement gas introduced into the main pumping means). Accordingly, the concentration of the predetermined gas component can be accurately and constantly controlled in the vicinity of the inner detecting electrode of the measuring pumping means or in the vicinity of the outer detecting electrode of the concentration-detecting means.

Therefore, the concentration of the predetermined gas component introduced into the measuring pumping means or the concentration-detecting means is scarcely affected by the change in oxygen concentration in the measurement gas (the measurement gas introduced into the main pumping means). As a result, the pumping current value detected by the current-detecting means or the electromotive force detected by the voltage-detecting means is not affected by the change in concentration of the predetermined gas component in the measurement gas. Thus a value is obtained, which accurately corresponds to the amount of the objective component existing in the measurement gas.

In the oxide sensor according to the present invention, the outer measuring electrode is arranged at a position exposed to a space into which the reference gas is introduced. Thus the oxygen contained in the measurement gas can be compared with the oxygen contained in the reference gas, making it possible to detect the oxides more accurately.

Especially, it is preferable that the outer measuring electrode and the outer detecting electrode are combined into a common unit. In this embodiment, a common electrode, which serves as both of the outer measuring electrode of the concentration-measuring means and the outer detecting electrode of the measuring pumping means or the concentration-detecting means, is exposed to the reference gas-introducing space. The common electrode can be defined as a reference electrode for the respective detecting processes performed by the concentration-measuring means, the measuring pumping means, and the concentration-detecting means. In accordance with this definition, the inner measuring electrode of the concentration-measuring means, and the inner detecting electrode of the measuring pumping means and the concentration-detecting means can be defined as a measuring electrode and a detecting electrode respectively.

The main pumping means may include the inner and outer pumping electrodes formed at the inside and the outside of a first chamber surrounded by substrates composed of solid electrolytes, for introducing the measurement gas thereinto, and the substrate interposed between the both electrodes.

The electric signal-generating conversion means may include the detecting electrode formed at the inside of a second chamber surrounded by substrates composed of solid electrolytes, for introducing the measurement gas thereinto after being subjected to the pumping process performed by the main pumping means, a reference electrode formed at the inside of a reference gas-introducing space surrounded by substrates composed of solid electrolytes, for introducing a reference gas thereinto, and the substrate interposed between the detecting electrode and the reference electrode.

The concentration-measuring means may include the measuring electrode formed at the inside of the first chamber surrounded by substrates composed of solid electrolytes, for introducing the measurement gas from the external space, the reference electrode formed in the reference gas-introducing space surrounded by substrates composed of solid electrolytes, for introducing the reference gas thereinto, and the substrate interposed between the measuring electrode and the reference electrode.

The oxide sensor constructed as described above may further comprise a first diffusion rate-determining section for giving a predetermined diffusion resistance to the measurement gas, provided at a passage for introducing the measurement gas from the external space into the first chamber, and a second diffusion rate-determining section for giving a predetermined diffusion resistance to the measurement gas, provided at a passage for introducing the measurement gas into the second chamber after being subjected to the pumping process performed by the main pumping means. In this embodiment, the first and second diffusion rate-determining sections may be composed of passages capable of giving predetermined diffusion resistances to the measurement gas respectively.

The oxide sensor constructed as described above may further comprise a third diffusion rate-determining section for giving a predetermined diffusion resistance to the measurement gas, provided at a passage for allowing the measurement gas in the second chamber to approach the detecting electrode.

Preferably, the solid electrolyte is an oxygen ion-conductive solid electrolyte based on the use of a ceramic such as $ZrO_2$. Preferably, a porous material capable of giving a predetermined diffusion resistance to the measurement gas is used for the first or second diffusion rate-determining section in order to provide designed desired states of the measurement gas in the first and second chambers.

It is preferable to use an Rh cermet for the oxide-decomposing catalyst for constructing the electrode or the catalyst arranged in the first and second chambers.

The inner pumping electrode and the measuring electrode provided in the first chamber may be arranged on the opposing substrates, or on an identical plane of any one of the substrates in the first chamber.

A plurality of second chambers linked to the first chamber may be arranged in series to or in parallel to the first chamber. The voltage applied between the electrodes or the electromotive force of the oxygen concentration cell generated between the electrodes may be individually set for the respective second chambers, depending on oxides as measurement objectives. Thus a plurality of oxides of different types can be measured by using one sensor.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

Several embodiments, in which the oxide sensor according to the present invention is applied to oxide sensors for measuring oxides contained in, for example, atmospheric air and exhaust gas discharged from vehicles or automobiles, such as NO, $NO_2$, $SO_2$, $CO_2$, and $H_2O$, will be explained below with reference to FIGS. 1 to 10.

Figure 1:
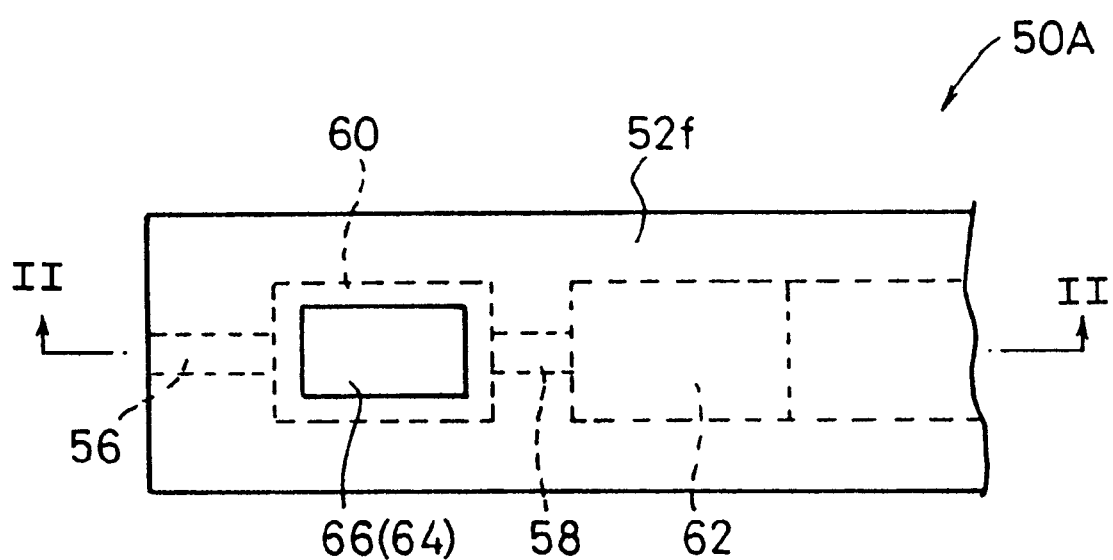
FIG. 1 shows a plan view illustrating an oxide sensor according to a first embodiment.
Figure 2:
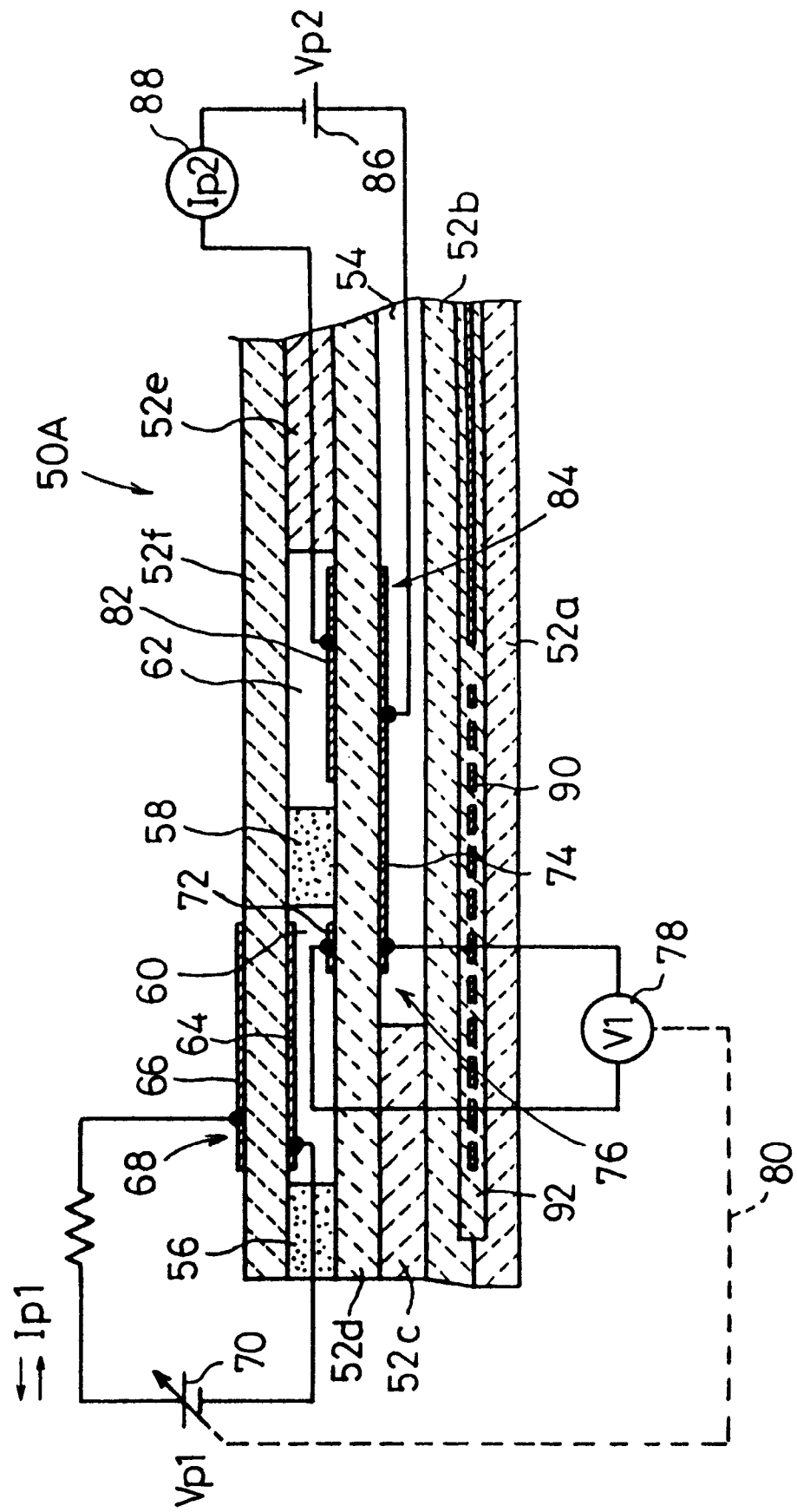
FIG. 2 shows a cross-sectional view taken along a line II—II in FIG. 1.

At first, as shown in FIGS. 1 and 2, an oxide sensor 50A according to a first embodiment has a lengthy plate-shaped configuration as a whole, comprising, for example, six stacked solid electrolyte layers 52a to 52f composed of ceramics based on the use of oxygen ion-conductive solid electrolytes such as $ZrO_2$. First and second layers from the bottom are designated as first and second substrate layers 52a, 52b respectively. Third and fifth layers from the bottom are designated as first and second spacer layers 52c, 52e respectively. Fourth and sixth layers from the bottom are designated as first and second solid electrolyte layers 52d, 52f respectively.

Specifically, the first spacer layer 52c is stacked on the second substrate layer 52b. The first solid electrolyte layer 52d, the second spacer layer 52e, and the second solid electrolyte layer 52f are successively stacked on the first spacer layer 52c.

A space (reference gas-introducing space 54), into which a reference gas such as atmospheric air to be used as a reference for measuring oxides is introduced, is formed between the second substrate layer 52b and the first solid electrolyte layer 52d, the space being comparted by a lower surface of the first solid electrolyte layer 52d, an upper surface of the second substrate layer 52b, and a side surface of the first spacer layer 52c.

The second spacer layer 52e is interposed between the first and second solid electrolyte layers 52d, 52f. First and second diffusion rate-determining sections 56, 58 are also interposed between the first and second solid electrolyte layers 52d, 52f.

A first chamber 60 for adjusting the partial pressure of oxygen in a measurement gas is formed and comparted by a lower surface of the second solid electrolyte layer 52f, side surfaces of the first and second diffusion rate-determining sections 56, 58, and an upper surface of the first solid electrolyte layer 52d. A second chamber 62 for finely adjusting the partial pressure of oxygen in the measurement gas and measuring oxides, for example, nitrogen oxides (NOx) in the measurement gas is formed and comparted by a lower surface of the second solid electrolyte layer 52f, a side surface of the second diffusion rate-determining section 58, a side surface of the second spacer layer 52e, and an upper surface of the first solid electrolyte layer 52d.

The external space communicates with the first chamber 60 through the first diffusion-rate determining section 56, and the first chamber 60 communicates with the second chamber 62 through the second diffusion rate-determining section 58.

The first and second diffusion-rate determining sections 56, 58 give predetermined diffusion resistances to the measurement gas to be introduced into the first and second chambers 60, 62 respectively. Each of the first and second diffusion-rate determining sections 56, 58 can be formed as a passage composed of, for example, a porous material, or a small hole having a predetermined cross-sectional area so that the measurement gas may be introduced.

Especially, the second diffusion-rate determining section 58 is arranged and filled with a porous material comprising, for example, $ZrO_2$. The diffusion resistance of the second diffusion-rate determining section 58 is made larger than the diffusion resistance of the first diffusion-rate determining section 56.

An atmosphere in the first chamber 60 is introduced into the second chamber 62 under the predetermined diffusion resistance through the second diffusion rate-determining section 58. Therefore, the oxide sensor 50A has the following directional characteristic. Namely, the measurement gas existing in the external space is introduced into the oxide sensor 50A in a direction of the first diffusion rate-determining section 56→the first chamber 60→the second diffusion rate-determining section 58→the second chamber 62. This direction can be defined as "downstream direction" for the measurement gas.

An inner pumping electrode 64, which is composed of a porous cermet electrode having a flat and substantially rectangular shape, is formed on an entire surface portion for forming the first chamber 60, of the lower surface of the second solid electrolyte layer 52f. An outer pumping electrode 66 is formed on a portion corresponding to the inner pumping electrode 64, of the upper surface of the second solid electrolyte layer 52f. An electrochemical pumping cell, i.e., a main pumping cell 68 is constructed by the inner pumping electrode 64, the outer pumping electrode 66, and the second solid electrolyte layer 52f interposed between the both electrodes 64, 66.

A desired control voltage (pumping voltage) Vp1 is applied between the inner pumping electrode 64 and the outer pumping electrode 66 of the main pumping cell 68 by the aid of an external variable power source 70 to allow a pumping current Ip1 to flow in a positive or negative direction between the outer pumping electrode 66 and the inner pumping electrode 64. Thus the oxygen in the atmosphere in the first chamber 60 can be pumped out to the external space at the outside, or the oxygen in the external space can be pumped into the first chamber 60.

A measuring electrode 72, which is composed of a porous cermet electrode having a flat and substantially rectangular shape, is formed on a portion adjacent to the second diffusion rate-determining section 58, of the upper surface of the first solid electrolyte layer 52d for forming the first chamber 60. A reference electrode 74 is formed on a portion exposed to the reference gas-introducing space 54, of the lower surface of the first solid electrolyte layer 52d. An electrochemical sensor cell, i.e., a controlling oxygen partial pressure-detecting cell 76 is constructed by the measuring electrode 72, the reference electrode 74, and the first solid electrolyte layer 52d.

An electromotive force is generated between the measuring electrode 72 and the reference electrode 74 of the controlling oxygen partial pressure-detecting cell 76 on the basis of a difference in oxygen concentration between the atmosphere in the first chamber 60 and the reference gas (atmospheric air) in the reference gas-introducing space 54. The partial pressure of oxygen in the atmosphere in the first chamber 60 can be detected by measuring the generated electromotive force by the aid of a voltmeter 78.

Namely, the voltage V1, which is generated between the reference electrode 74 and the measuring electrode 72, is an electromotive force of the oxygen concentration cell, generated on the basis of a difference between a partial pressure of oxygen in the reference gas introduced into the reference gas-introducing space 54 and a partial pressure of oxygen in the measurement gas in the first chamber 60. The voltage V1 has the following relationship known as the Nernst's equation.

$$V1 = RT/4F \cdot \ln(P1(O_2)/P0(O_2))$$

R: gas constant;
T: absolute temperature;
F: Faraday constant;
$P1(O_2)$: partial pressure of oxygen in the first chamber 60;
$P0(O_2)$: partial pressure of oxygen in the reference gas.

Therefore, the partial pressure of oxygen in the first chamber 60 can be detected by measuring the voltage V1 generated on the basis of the Nernst's equation, by the aid of the voltmeter 78.

The detected value of the partial pressure of oxygen is used to control the pumping voltage of the variable power source 70 by the aid of a feedback control system 80. Specifically, the pumping operation performed by the main pumping cell 68 is controlled so that the partial pressure of oxygen in the first chamber 60 has a predetermined value which is sufficiently low to control the partial pressure of oxygen in the second chamber 62 in the next step.

Figure 3:
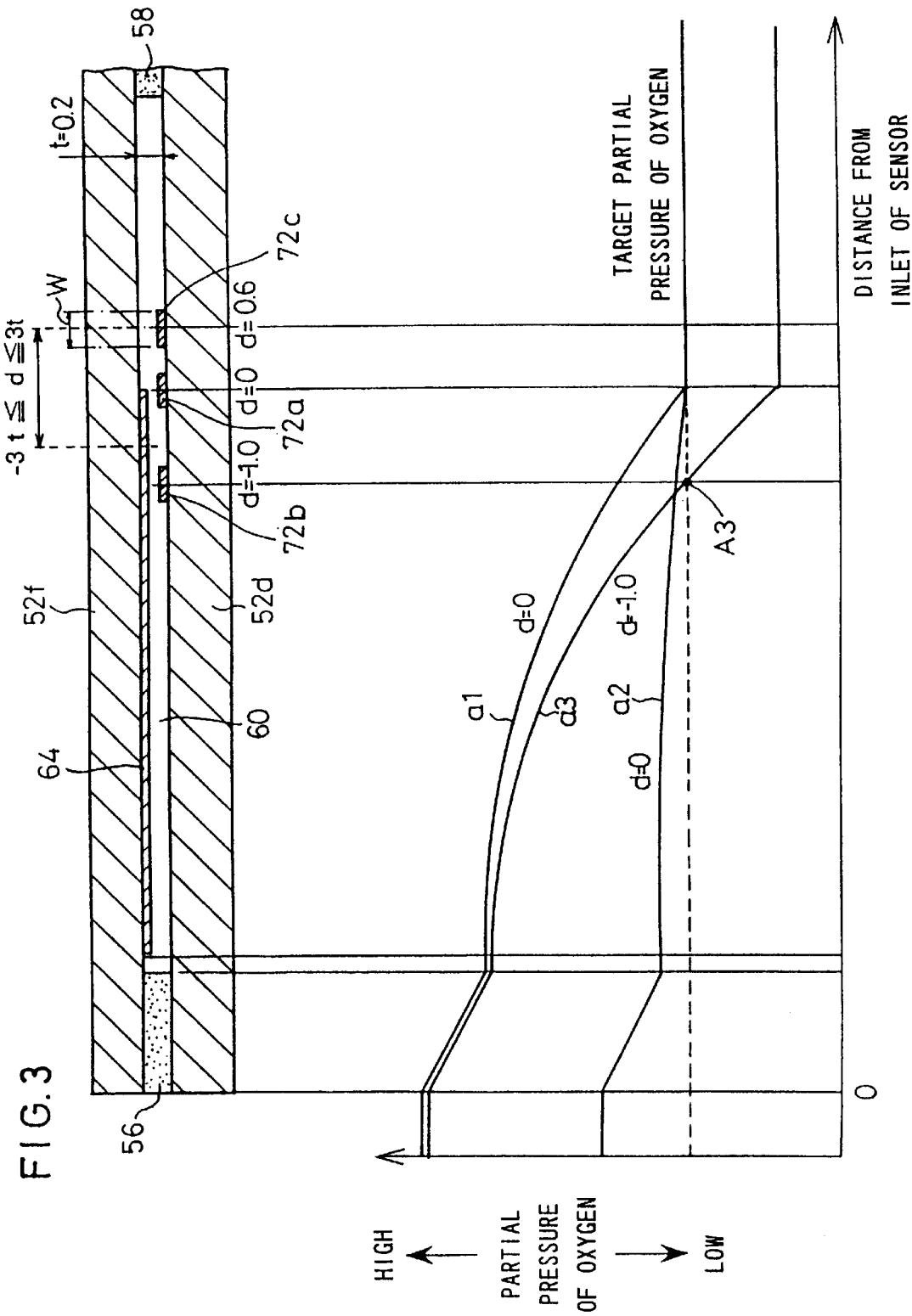
FIG. 3 illustrates relationships between the arrangement of a measuring electrode with respect to an inner pumping electrode and the partial pressure of oxygen introduced into a second chamber, concerning the oxide sensor according to the first embodiment.

Especially, as shown in FIG. 3, the width w of the measuring electrode 72 along the downstream direction is defined to be a predetermined length, in the oxide sensor 50A according to the first embodiment. Specifically, the width w of the measuring electrode 72 is defined to be a length considering the object to suppers decomposition of the oxides as the measurement objective in the first chamber 60, and an appropriate size for printing to make it possible to produce the oxide sensor 50A based on the use of the screen printing technique. Namely, as shown in FIG. 3, the width w of the measuring electrode 72 is restricted to be in a range of w≦5t provided that the height of the first chamber 60 is represented by t. Further, in order to ensure the accuracy for the partial pressure of oxygen measured by the controlling oxygen partial pressure-detecting cell 76 in the oxide sensor 50A according to the first embodiment, the relative arrangement of the measuring electrode 72 is defined as follows in relation to the inner pumping electrode 64 of the main pumping cell 68.

Namely, as shown in FIG. 3, the measuring electrode 72 is arranged at a position at which the projective distance d from a downstream end of the inner pumping electrode 64 (the end located on a side of the second diffusion rate-determining section 58) to a center of the measuring electrode 72 satisfies at least $-3t \leq d$ (t: height of the first chamber 60). Preferably, the measuring electrode 72 is arranged to satisfy $-3t \leq d \leq 3t$.

The inner pumping electrode 64 and the outer pumping electrode 66 are composed of an inactive material having a low catalytic activity on NOx, for example, NO in the measurement gas introduced in the first chamber 60. Specifically, the inner pumping electrode 64 and the outer pumping electrode 66 can be composed of a porous cermet electrode. In this embodiment, they are formed of a metal such as Pt and a ceramic such as $ZrO_2$. Especially, it is necessary, for the inner pumping electrode 64 and the measuring electrode 72 arranged in the first chamber 60 contacting with the measurement gas, to use a material having a weak reducing ability or no reducing ability with respect to the NO components in the measurement gas. It is preferable that the inner pumping electrode 64 and the measuring electrode 72 are composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

As shown in FIG. 2, the gas sensor 50A according to the first embodiment includes a detecting electrode 82 composed of a porous cermet electrode having a flat and substantially rectangular shape. The detecting electrode 82 is formed on a portion separated from the second diffusion rate-determining section 58, of the upper surface of the first solid electrolyte layer 52*d* for forming the second chamber 62. An electrochemical pumping cell, i.e., a measuring pumping cell 84 is constructed by the detecting electrode 82, the reference electrode 74, and the first solid electrolyte layer 52*d*.

The detecting electrode 82 can be constructed by appropriately selecting an oxide-decomposing catalyst, for example, an Rh cermet, a material having a low catalytic activity, or a combination of an oxide-decomposing catalyst arranged in the vicinity of a material having a low catalytic activity. In the first embodiment, the detecting electrode 82 is composed of a porous cermet comprising Rh as a metal capable of reducing NOx as the measurement gas component, and zirconia as a ceramic. Thus the detecting electrode 82 functions as a NOx-reducing catalyst for reducing NOx existing in the atmosphere in the second chamber 62. Moreover, the oxygen in the atmosphere in the second chamber 62 can be pumped out to the reference gas-introducing space 54 by applying a constant voltage Vp2 between the detecting electrode 82 and the reference electrode 74 by the aid of a DC power source 86. A pumping current Ip2, which is allowed to flow in accordance with the pumping operation performed by the measuring pumping cell 84, is detected by an ammeter 88.

The gas sensor 50A according to the first embodiment includes a heater 90 for generating heat in accordance with electric power supply from the outside. The heater 90 is embedded in a form of being vertically interposed between the first and second substrate layers 52*a*, 52*b*. The heater 90 is provided in order to increase the conductivity of oxygen ion. A ceramic layer 92 composed of alumina or the like is formed to cover upper and lower surfaces of the heater 90 so that the heater 90 is electrically insulated from the first and second substrate layers 52*a*, 52*b*.

As shown in FIG. 2, the heater 90 is arranged to extend over an entire region ranging from the first chamber 60 to the second chamber 62. Thus the first and second chambers 60, 62 are heated to predetermined temperatures respectively. Further, the main pumping cell 68, the controlling oxygen partial pressure-detecting cell 76, and the measuring pumping cell 84 are also heated to and maintained at predetermined temperatures respectively.

The oxide sensor 50A according to the first embodiment is basically constructed as described above. Next, its function and effect will be explained.

Before the measurement of oxides, the oxide sensor 50A according to the first embodiment is set in a state in which the measurement gas can be introduced into the first chamber 60. Next, an electric power is applied to the heater 90 so that the first and second solid electrolyte layers 52*d*, 52*f* for the first chamber 60 of the oxide sensor 50A are heated to, for example, 400° C. to 900° C., and the first and second solid electrolyte layers 52*d*, 52*f* for the second chamber 62 are heated to, for example, 700° C. to 900° C. After the oxide sensor 50A is heated in such a temperature state, the first and second solid electrolyte layers 52*d*, 52*f* are activated in a desired state.

Next, the measurement of oxides such as NOx contained in the measurement gas is started by introducing the measurement gas into the oxide sensor 50A having been set as described above. The measurement gas is introduced into the first chamber 60 under a predetermined diffusion resistance through the first diffusion rate-determining section 56. The partial pressure of oxygen contained in the measurement gas is controlled to have a predetermined value in accordance with a predetermined pumping voltage Vp1 applied between the outer pumping electrode 66 and the inner pumping electrode 64 by the aid of the variable power source 70. Namely, the partial pressure of oxygen in the first chamber 60 can be measured on the basis of a voltage V1 between the reference electrode 74 and the measuring electrode 72, detected by the voltmeter 78. The voltage V1 is an electromotive force of the oxygen concentration cell defined by the Nernst's equation described above. The pumping voltage Vp1 applied by the variable power source 70 is controlled by the aid of the feedback control system 80 so that the voltage V1 is 180 mV to 350 mV. Thus the partial pressure of oxygen in the first chamber 60 is controlled to have a predetermined value.

The measurement gas, which has been controlled to have the predetermined partial pressure of oxygen in the first chamber 60, is introduced into the second chamber 62 through the second diffusion rate-determining section 58 designed to have a diffusion resistance larger than that of the first diffusion rate-determining section 56.

A predetermined pumping voltage Vp2, which makes it possible to sufficiently pump out the oxygen in the second chamber 62, is applied between the reference electrode 74 and the detecting electrode 82 in the second chamber 62. Owing to the pumping voltage Vp2, NOx contained in the measurement gas, such as NO and $NO_2$, is decomposed by the detecting electrode 82 which serves as an oxide-decomposing catalyst comprising the Rh cermet. Alternatively, NOx is decomposed by a catalyst existing separately from the detecting electrode 82. The oxygen thus produced is pumped out toward the reference gas-introducing space 54 through the first solid electrolyte layer 52d. In this process, a current value Ip2, which is generated by movement of oxygen ion, is measured by the ammeter 88. The concentration of predetermined oxides, for example, NOx such as NO and $NO_2$ contained in the measurement gas is determined from the current value Ip2.

Especially, the relative arrangement of the inner pumping electrode 64 and the measuring electrode 72 for the first chamber 60 is set to satisfy the predetermined range ($-3t \leq d \leq 3t$) as shown in FIG. 3, in the oxide sensor 50A according to the first embodiment. Accordingly, the measurement gas can be supplied to the second chamber 62, while controlling the partial pressure of oxygen with a high degree of accuracy. Thus the oxides can be measured highly accurately by the aid of the measuring pumping cell 84.

FIG. 3 schematically shows the relationship between the arrangement of the measuring electrode 72 with respect to the inner pumping electrode 64 and the partial pressure of oxygen of the measurement gas introduced into the second chamber 62.

It is assumed, for example, the partial pressure of oxygen is measured by using a measuring electrode 72a (d=0) arranged to allow its center to coincide with the downstream end of the inner pumping electrode 64 (the end located on the side of the second chamber 62), and the pumping voltage Vp1 applied between the inner pumping electrode 64 and the outer pumping electrode 66 is controlled on the basis of the measured partial pressure of oxygen. When the measurement gas introduced into the first chamber 60 has a high partial pressure of oxygen before introduction, the partial pressure of oxygen is promptly lowered owing to the operation of the inner pumping electrode 64 as indicated by a characteristic curve a1, and then the measurement gas having a desired target partial pressure of oxygen is supplied to the second chamber 62. When the partial pressure of oxygen of the measurement gas before introduction is lowered under the same condition as described above (d=0), the operation of the inner pumping electrode 64 is weak, and the partial pressure of oxygen is lowered gradually and slowly as indicated by a characteristic curve a2. After that, the measurement gas having the desired partial pressure of oxygen is supplied to the second chamber 62 in the same manner as described above.

Next, it is assumed that the partial pressure of oxygen is measured by using a measuring electrode 72b arranged by deviating the center by d=−1.0 mm (t=0.2 mm) from the downstream end of the inner pumping electrode 64 toward the first diffusion rate-determining section 56, and the pumping voltage Vp1 applied between the inner pumping electrode 64 and the outer pumping electrode 66 is controlled on the basis of the measured partial pressure of oxygen. When the measurement gas introduced into the first chamber 60 has a high partial pressure of oxygen before introduction, the partial pressure of oxygen is promptly lowered owing to the operation of the inner pumping electrode 64 as indicated by a characteristic curve a3. However, the measuring point for the partial pressure of oxygen is located at a position corresponding to an intermediate portion of the inner pumping electrode 64. Therefore, the control is performed so that the partial pressure of oxygen at the position at which the measuring electrode 72b is arranged, i.e., the partial pressure of oxygen at a point A3 coincides with the target partial pressure of oxygen. In this case, the partial pressure of oxygen is further lowered by a residual portion of the inner pumping electrode 64 located downstream from the portion at which the measuring electrode 72b is arranged. Therefore, the measurement gas is supplied to the second chamber 62 in a state in which the partial pressure of oxygen is lower than the target partial pressure of oxygen.

Even when the partial pressure of oxygen of the measurement gas before introduction is lowered under the same condition as described above (d=−1.0 mm), the control is performed so that the partial pressure of oxygen coincides with the target partial pressure of oxygen at the point A3. Therefore, the measurement gas is supplied to the second chamber 62 in a state in which the partial pressure of oxygen has a value lower than the desired partial pressure of oxygen, although the partial pressure of oxygen is not lowered so much as compared with the case represented by the characteristic curve a3 described above.

On the other hand, it is assumed that the partial pressure of oxygen is measured by using a measuring electrode 72c arranged by deviating the center by more than 0.6 mm (t=0.2 mm) from the downstream end of the inner pumping electrode 64 toward the second diffusion rate-determining section 58, and the pumping voltage Vp1 applied between the inner pumping electrode 64 and the outer pumping electrode 66 is controlled on the basis of the measured partial pressure of oxygen. Under this condition, a phenomenon occurs, in which oscillation or shortage of gain is caused due to response delay in the feedback loop comprising the inner pumping electrode 64 and the measuring electrode 72c, and consequently the partial pressure of oxygen of the measurement gas supplied to the second chamber 62 is deviated from the target value.

Figure 4:
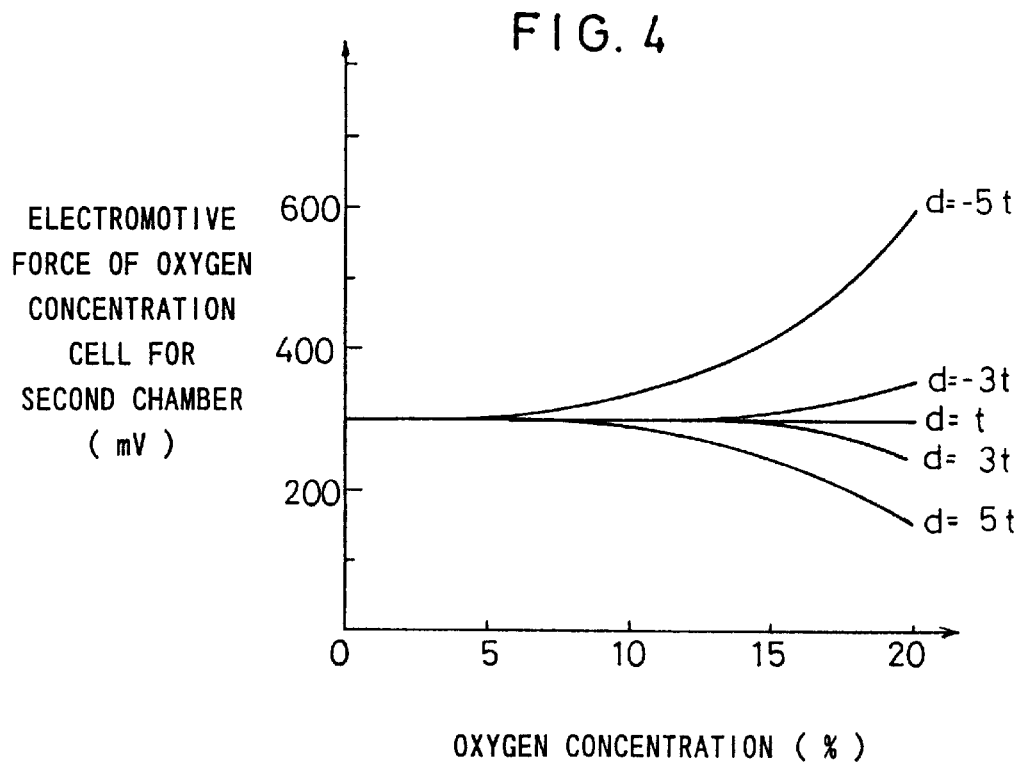
FIG. 4 shows characteristics of the oxide sensor according to the first embodiment, illustrating relationships between the oxygen concentration before introduction into a first chamber and the electromotive force of an oxygen concentration cell measured in the second chamber, obtained by changing the position of arrangement of the measuring electrode.

FIG. 4 shows results obtained by measuring the electromotive force of the oxygen concentration cell for the second chamber 62, while setting the position of the measuring electrode 72 in a range of d=5t to −5t, adjusting the voltage V1 at 300 mV as the electromotive force of the oxygen concentration cell including the measuring electrode 72 for the first chamber 60, and changing the concentration of $O_2$ contained in the measurement gas.

According to the results, when the concentration of $O_2$ in the measurement gas is high, the oxygen concentration in the second chamber 62 is increased (the electromotive force of the oxygen concentration cell for the second chamber 62 is decreased), as the position of arrangement of the measuring electrode 72 becomes to be separated from the downstream end of the inner pumping electrode 64 in the direction toward the second chamber 62. On the other hand, when the concentration of $O_2$ in the measurement gas is high, the oxygen concentration in the second chamber 62 is decreased (the electromotive force of the oxygen concentration cell for the second chamber 62 is increased), as the position of arrangement of the measuring electrode 72 is moved inward from the downstream end of the inner pumping electrode 64 toward the first diffusion rate-determining section 56. Therefore, if the measuring electrode 72 is displaced by more than the predetermined amount, for example, if the measuring electrode 72 is displaced by more than d=−3t from the downstream end of the inner pumping electrode 64 toward the first diffusion rate-determining section 56, the partial pressure of oxygen in the first chamber 60 is excessively lowered. As a result, the decomposition reactions of the oxides as the measurement objective are brought about on the inner pumping electrode 64.

Figure 5:
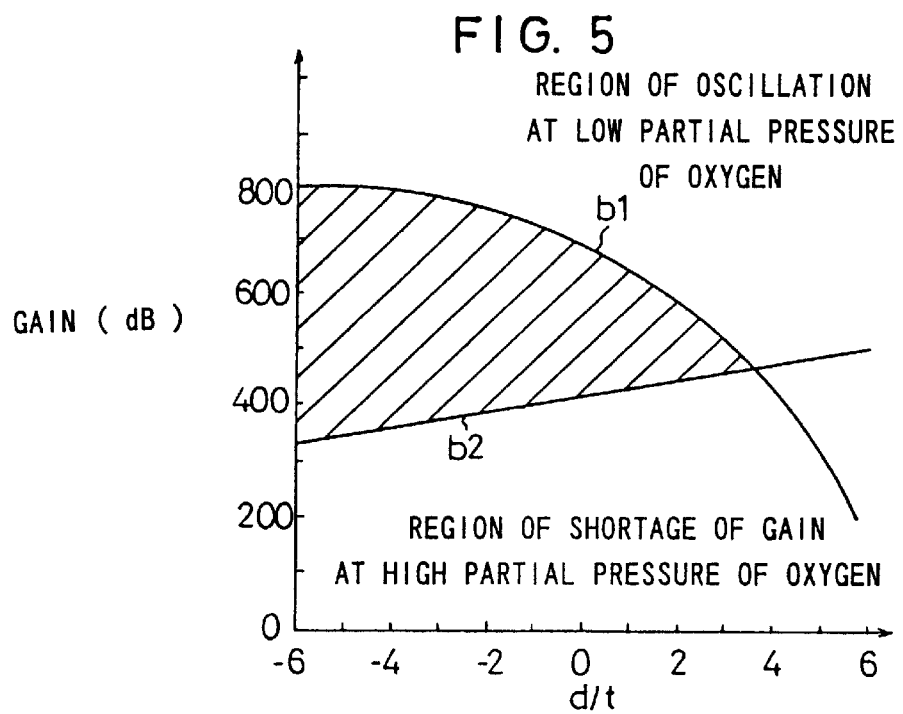
FIG. 5 shows characteristics of the oxide sensor according to the first embodiment, illustrating relationships concerning the feedback gain at low and high partial pressures of oxygen, obtained by changing the position of arrangement of the measuring electrode.

FIG. 5 shows results obtained by measuring the gain of the feedback control system 80 for the first chamber 60 by using a measurement gas containing $O_2$ at a high concentration, and the oscillation-generating gain of the feedback control system 80 for the first chamber 60 by using a measurement gas containing $O_2$ at a low concentration. In the case of the measurement gas containing $O_2$ at a high concentration, the shortage of gain occurs in a region below a characteristic curve b1, and the response delay takes place.

On the other hand, in the case of the measurement gas containing $O_2$ at a low concentration, the oscillation occurs in a region above a characteristic curve b2, and it is impossible to stably set the partial pressure of oxygen. Therefore, considering the foregoing facts, the feedback control can be performed while maintaining a constant gain without depending on the oxygen concentration of the measurement gas, by setting the gain within a range indicated by hatched lines in FIG. 5. It is derived that the position of the measuring electrode 72, which enables the control described above, resides in the distance of $d \leq 3t$ with respect to the end of the inner pumping electrode 64.

According to the results described above, the distance d of the measuring electrode 72 is allowed to satisfy $-3t \leq d \leq 3t$ with respect to the downstream end of the inner pumping electrode 64, i.e., the end located on the side of the second diffusion rate-determining section 58. Thus the objective components in the measurement gas can be supplied to the second chamber 62 without causing any decomposition, while allowing the measurement gas to have an optimum partial pressure of oxygen.

Next, an oxide sensor 50B according to a second embodiment will be explained with reference to FIG. 6. Components or parts of the oxide sensor 50B corresponding to those shown in FIG. 2 are designated by the same reference numerals, duplicate explanation of which will be omitted.

Figure 6:
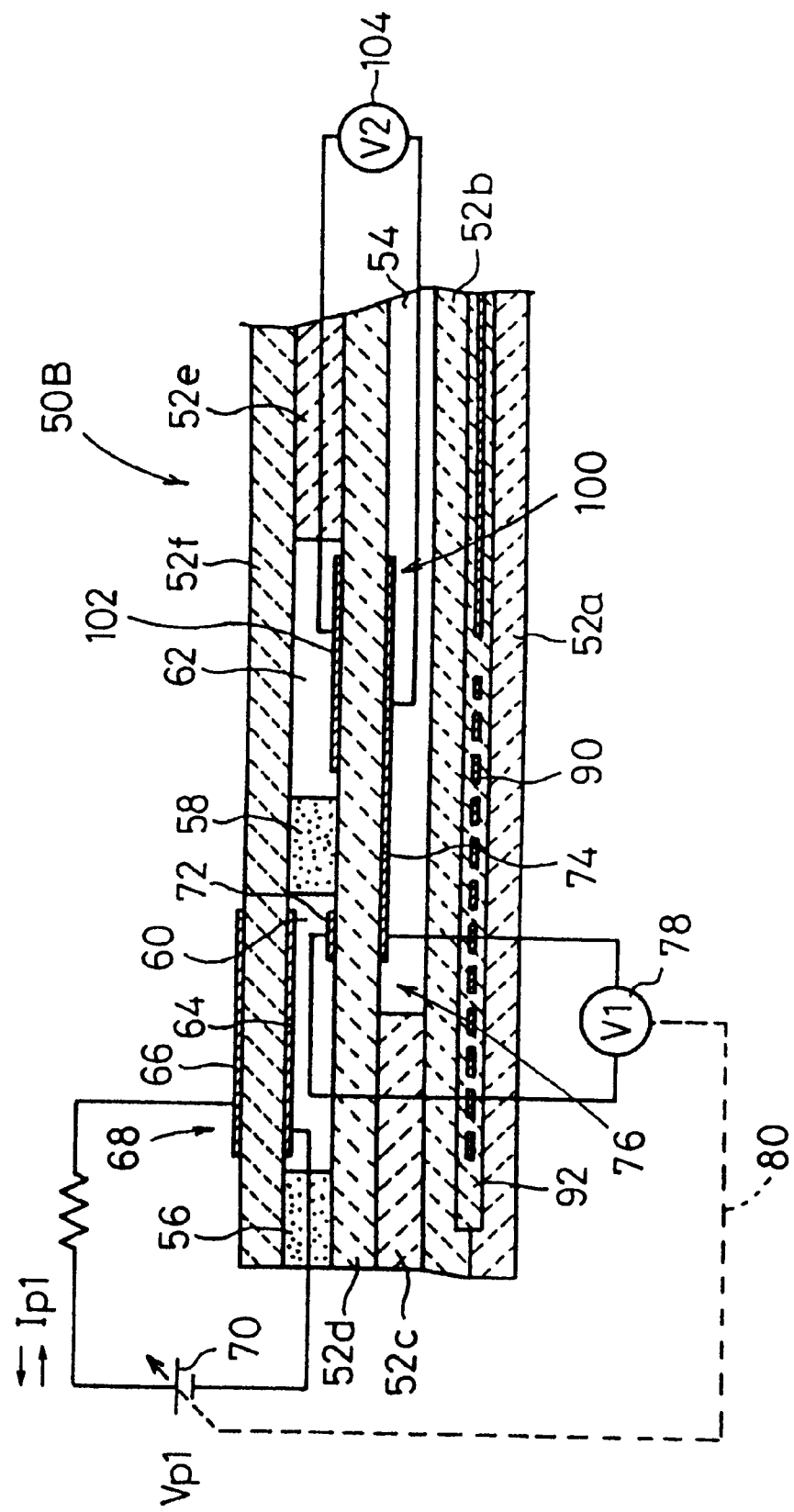
FIG. 6 shows a cross-sectional view illustrating an oxide sensor according to a second embodiment.

As shown in FIG. 6, the oxide sensor 50B according to the second embodiment has approximately the same structure as that of the oxide sensor 50A according to the first embodiment (see FIG. 2). However, the former is different from the latter in that a measuring oxygen partial pressure-detecting cell 100 is provided in place of the measuring pumping cell 84.

The measuring oxygen partial pressure-detecting cell 100 comprises a detecting electrode 102 formed on a portion for forming the second chamber 62, of the upper surface of the first solid electrolyte layer 52d, the reference electrode 74 formed on the lower surface of the first solid electrolyte layer 52d, and the first solid electrolyte layer 52d.

In this embodiment, an electromotive force (electromotive force of an oxygen concentration cell) V2 is generated between the detecting electrode 102 and the reference electrode 74 of the measuring oxygen partial pressure-detecting cell 100, corresponding to a difference in oxygen concentration between an atmosphere around the detecting electrode 102 and an atmosphere around the reference electrode 74.

Therefore, the partial pressure of oxygen in the atmosphere around the detecting electrode 102, in other words, the partial pressure of oxygen defined by oxygen produced by reduction or decomposition of the measurement gas components (NOx) is detected as a value of the voltage V2 by measuring the electromotive force (voltage) V2 generated between the detecting electrode 102 and the reference electrode 74.

The degree of change in electromotive force V2 represents the NO concentration. Namely, the electromotive force V2, which is outputted from the measuring oxygen partial pressure-detecting cell 100 constructed by the detecting electrode 102, the reference electrode 74, and the first solid electrolyte layer 52d, represents the NO concentration in the measurement gas.

In the oxide sensor 50B according to the second embodiment, the width w of the measuring electrode 72 along the downstream direction of the controlling oxygen partial pressure-detecting cell 76 is also restricted to be in a range of $w \leq 5t$ provided that the height of the first chamber 60 is represented by t, in the same manner as the oxide sensor 50A according to the first embodiment. Further, the measuring electrode 72 is arranged at the position at which the projective distance d from the downstream end of the inner pumping electrode 64 (the end located on the side of the second diffusion rate-determining section 58) to the center of the measuring electrode 72 satisfies at least $-3t \leq d$. Preferably, the measuring electrode 72 is arranged to satisfy $-3t \leq d \leq 3t$.

Therefore, in the oxide sensor 50B according to the second embodiment, the objective components in the measurement gas can be supplied to the second chamber 62 without causing any decomposition, while allowing the measurement gas to have an optimum partial pressure of oxygen. Thus the oxides can be measured with a high degree of accuracy by the aid of the measuring oxygen partial pressure-detecting cell 100.

Next, an oxide sensor 50C according to a third embodiment will be explained with reference to FIG. 7. Components or parts of the oxide sensor 50C corresponding to those shown in FIG. 2 are designated by the same reference numerals, duplicate explanation of which will be omitted.

Figure 7:
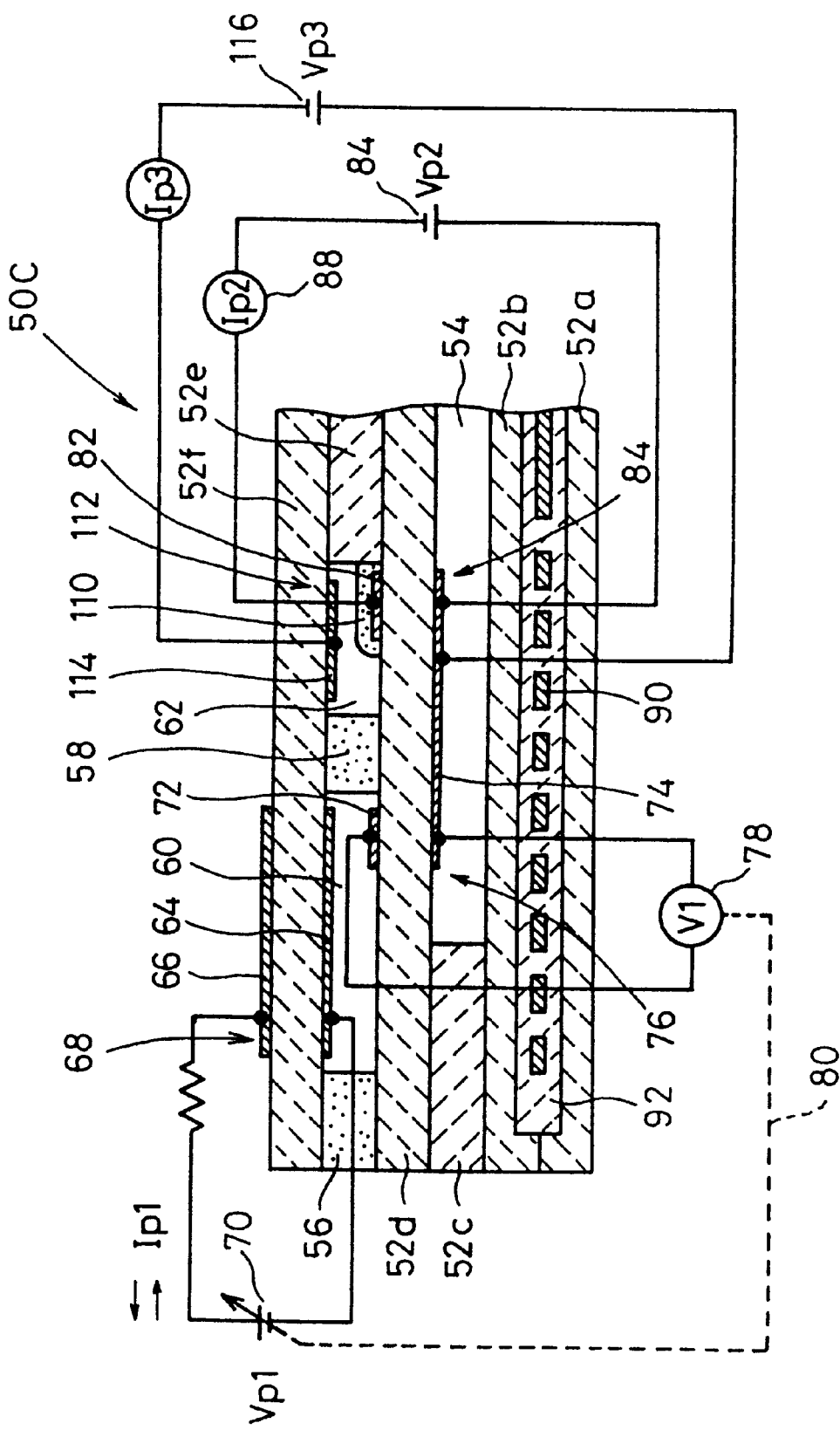
FIG. 7 shows a cross-sectional view illustrating an oxide sensor according to a third embodiment.

As shown in FIG. 7, the oxide sensor 50C according to the third embodiment has approximately the same structure as that of-the oxide sensor 50A according to the first embodiment. However, the former is different from the latter in that a porous $Al_2O_3$ layer or a porous $ZrO_2$ layer for constructing a third diffusion rate-determining section 110 is formed to cover the detecting electrode 82, and an auxiliary pumping cell 112 is provided.

The auxiliary pumping cell 112 comprises an auxiliary pumping electrode 114 composed of a porous cermet electrode having a flat and substantially rectangular shape and formed on an entire surface portion for forming the second chamber 62, of the lower surface of the second solid electrolyte layer 52f, the reference electrode 74, the second solid electrolyte layer 52f, the second spacer layer 52e, and the first solid electrolyte layer 52d.

The auxiliary pumping electrode 114 is constructed by using a material having a weak reducing ability or no reducing ability with respect to the NO components in the measurement gas, in the same manner as the inner pumping electrode 64 of the main pumping cell 68. In this embodiment, it is preferable that the auxiliary pumping electrode 114 is composed of, for example, a compound having the perovskite structure such as $La_3CuO_4$, a cermet comprising a ceramic and a metal having a low catalytic activity such as Au, or a cermet comprising a ceramic, a metal of the Pt group, and a metal having a low catalytic activity such as Au. Further, when an alloy comprising Au and a metal of the Pt group is used as an electrode material, it is preferable to add Au in an amount of 0.03 to 35 vol % of the entire metal components.

A desired constant voltage Vp3 is applied between the auxiliary pumping electrode 114 and the reference electrode 74 of the auxiliary pumping cell 112 by the aid of an external power source 116. Thus the oxygen in the atmosphere in the second chamber 62 can be pumped out to the reference gas-introducing space 54.

Accordingly, the partial pressure of oxygen in the atmosphere in the second chamber 62 is in a situation in which the measurement gas components (NOx) are not substantially reduced or decomposed, while giving a low value of the partial pressure of oxygen at which the measurement of the amount of the objective components is not substantially affected. In this embodiment, the change in amount of oxygen introduced into the second chamber 62 is greatly reduced as compared with the change which occurs in the measurement gas, owing to the operation of the main pumping cell 68 in the first chamber 60. Therefore, the partial pressure of oxygen in the second chamber 62 is controlled accurately and constantly.

The oxide sensor 50C according to the third embodiment includes the constant voltage (DC) power source 86. NOx flows into the measuring pumping cell 84 while being limited by the third diffusion rate-determining section 110. Under this condition, the constant voltage (DC) power source 86 is capable of applying a voltage having a magnitude to give a limiting current for pumping to be performed for oxygen produced during decomposition in the measuring pumping cell 84.

Therefore, in the oxide sensor 50C according to the third embodiment constructed as described above, the measurement gas, which has been controlled for its partial pressure of oxygen in the second chamber 62, is introduced into the detecting electrode 82 under a predetermined diffusion resistance through the third diffusion rate-determining section 110.

When it is intended to control the partial pressure of oxygen in the atmosphere in the first chamber 60 to have a low value of the partial pressure of oxygen which does not substantially affect the measurement of NOx, by operating the main pumping cell 68, in other words, when the pumping voltage Vp1 of the variable power source 70 is adjusted by the aid of the feedback control system 80 so that the voltage V1 detected by the controlling oxygen partial pressure-detecting cell 76 is constant, if the oxygen concentration in the measurement gas greatly changes, for example, in a range of 0 to 20%, then the respective partial pressures of oxygen in the atmosphere in the second chamber 62 and in the atmosphere in the vicinity of the detecting electrode 82 slightly change in ordinary cases. This phenomenon is caused probably because of the following reason. Namely, when the oxygen concentration in the measurement gas increases, the distribution of the oxygen concentration occurs in the widthwise direction and the thickness direction in the first chamber 60 over the measuring electrode 72. The distribution of the oxygen concentration changes depending on the oxygen concentration in the measurement gas.

However, in the case of the gas sensor 50C according to the third embodiment, the auxiliary pumping cell 112 is provided for the second chamber 62 so that the partial pressure of oxygen in its internal atmosphere always has a constant low value of the partial pressure of oxygen. Accordingly, even when the partial pressure of oxygen in the atmosphere introduced from the first chamber 60 to the second chamber 62 changes depending on the oxygen concentration in the measurement gas, the partial pressure of oxygen in the atmosphere in the second chamber 62 can be always made to have a constant low value, owing to the pumping operation performed by the auxiliary pumping cell 112. As a result, the partial pressure of oxygen can be controlled to have a low value at which the measurement of NOx is not substantially affected.

NOx in the measurement gas introduced into the detecting electrode 82 is reduced or decomposed around the detecting electrode 82. Thus, for example, a reaction of NO→½N₂+½O₂ is allowed to occur. In this process, a predetermined voltage Vp2, for example, 430 mV (700° C.) is applied between the detecting electrode 82 and the reference electrode 74 for constructing the measuring pumping cell 84, in a direction to pump out the oxygen from the second chamber 62 to the reference gas-introducing space 54.

Therefore, the pumping current Ip2 flowing through the measuring pumping cell 84 has a value which is proportional to a sum of the oxygen concentration in the atmosphere introduced into the second chamber 62, i.e., the oxygen concentration in the second chamber 62 and the oxygen concentration produced by reduction or decomposition of NOx by the aid of the detecting electrode 82.

In this embodiment, the oxygen concentration in the atmosphere in the second chamber 62 is controlled to be constant by means of the auxiliary pumping cell 112. Accordingly, the pumping current Ip2 flowing through the measuring pumping cell 84 is proportional to the NOx concentration. The NOx concentration corresponds to the amount of diffusion of NOx limited by the third diffusion rate-determining section 110. Therefore, even when the oxygen concentration in the measurement gas greatly changes, it is possible to accurately measure the NOx concentration, based on the use of the measuring pumping cell 84 by the aid of the ammeter 88.

It is assumed, for example, that the partial pressure of oxygen in the atmosphere in the second chamber 62 controlled by the auxiliary pumping cell 112 is 0.02 ppm, and the concentration of NO as the NOx component in the measurement gas is 100 ppm. The pumping current Ip2 flows in an amount corresponding to a sum (=50.02 ppm) of an oxygen concentration of 50 ppm produced by reduction or decomposition of NO and the oxygen concentration of 0.02 ppm in the atmosphere in the second chamber 62. Therefore, almost all of the pumping current value Ip2 obtained by operating the measuring pumping cell 84 represents the amount brought about by the reduction or decomposition of NO. Accordingly, the obtained result does not depend on the oxygen concentration in the measurement gas.

Next, an oxide sensor 50D according to a fourth embodiment will be explained with reference to FIG. 8. Components or parts of the oxide sensor 50D corresponding to those shown in FIGS. 6 and 7 are designated by the same reference numerals, duplicate explanation of which will be omitted.

Figure 8:
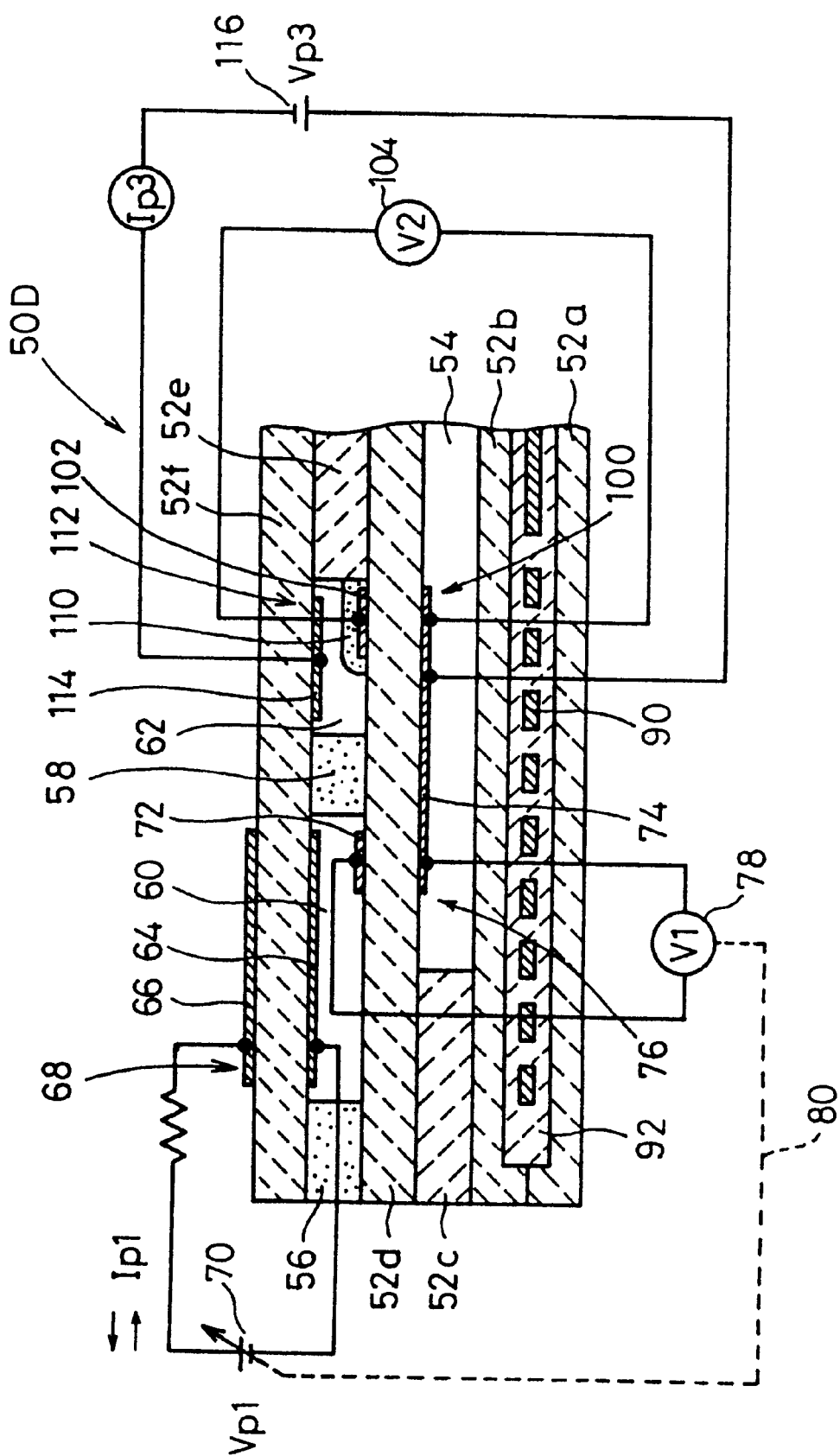
FIG. 8 shows a cross-sectional view illustrating an oxide sensor according to a fourth embodiment.

As shown in FIG. 8, the oxide sensor 50D according to the fourth embodiment has approximately the same structure as that of the oxide sensor 50B according to the second embodiment (see FIG. 6). However, the former is different from the latter in that a porous $Al_2O_3$ layer or a porous $ZrO_2$ layer for constructing a third diffusion rate-determining section 110 is formed to cover the detecting electrode 102 of the measuring oxygen partial pressure-detecting cell 100, and an auxiliary pumping cell 112 is provided, in the same manner as the oxide sensor 50C according to the third embodiment (see FIG. 7).

In this embodiment, the partial pressure of oxygen in the atmosphere in the second chamber 62 is in a situation in which the measurement gas components (NOx) are not substantially reduced or decomposed, while giving a low value of the partial pressure of oxygen at which the measurement of the amount of the objective components is not substantially affected, in the same manner as the oxide sensor 50C according to the third embodiment. The change in amount of oxygen introduced into the second chamber 62 is greatly reduced as compared with the change which occurs in the measurement gas, owing to the operation of the main pumping cell 68 in the first chamber 60. Therefore, the partial pressure of oxygen in the second chamber 62 is controlled accurately and constantly.

Therefore, even when the oxygen concentration in the measurement gas greatly changes, it is possible to accurately measure the NOx concentration, based on the use of the measuring oxygen partial pressure-detecting cell 100 by the aid of the voltmeter 104.

Figure 9:
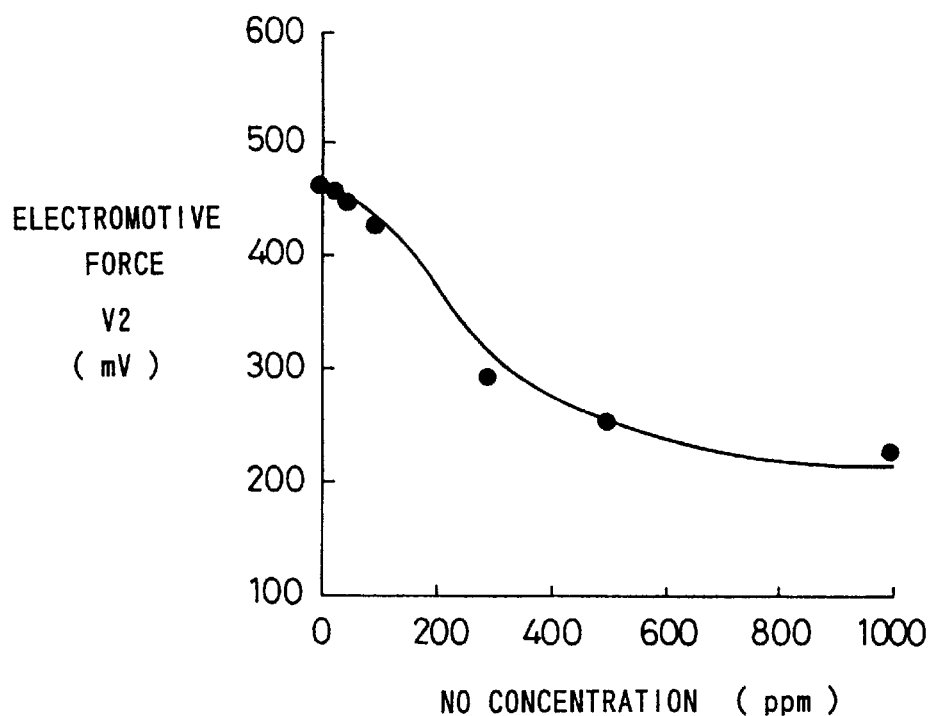
FIG. 9 shows a characteristic of the oxide sensor according to the fourth embodiment, illustrating the change in electromotive force generated in a measuring oxygen partial pressure-detecting means depending on the change in NO concentration.

Now, the principle of detection performed by the oxide sensor 50D according to the fourth embodiment will be explained with reference to FIG. 9 illustrating a characteristic of the oxide sensor 50D.

At first, when the NO concentration in the external space is 0 ppm, the pumping voltage Vp1 of the main pumping cell 68 is controlled so that the partial pressure of oxygen in the first chamber 60 is maintained to be $1.3 \times 10^{-7}$ atm, i.e., to give a value of the electromotive force V1=about 300 mV.

Next, the set voltage Vp3 applied to the auxiliary pumping cell 112 is set to be 460 mV. The partial pressure of oxygen in the second chamber 62 is controlled to be $6.1 \times 10^{-11}$ atm owing to the operation performed by the auxiliary pumping cell 112. As a result, the electromotive force V2 between the detecting electrode 102 and the reference electrode 74 of the measuring oxygen partial pressure-detecting cell 100 is about 460 mV. In this case, the inflammable gas components are oxidized in the first chamber 60, and the sensitivity to NOx is not affected thereby, because the partial pressure of oxygen in the first chamber 60 is $1.3 \times 10^{-7}$ atm, regardless of the fact that the partial pressure of oxygen in the second chamber 62 is $6.1 \times 10^{-11}$ atm.

If the NO concentration in the external space gradually increases, the reduction or decomposition reaction of NO is caused on the detecting electrode 102, because the detecting electrode 102 also functions as a Nox-reducing catalyst in the same manner as the detecting electrode 82 of the measuring pumping cell 84 described above (see FIG. 2). As a result, the oxygen concentration in the atmosphere around the detecting electrode 102 is increased. Accordingly, the electromotive force V2 generated between the detecting electrode 102 and the reference electrode 74 is gradually decreased. With reference to FIG. 9 illustrating the characteristic of the oxide sensor 50D, for example, when the NO concentration increases to 300 ppm, 500 ppm, and 1000 ppm, the electromotive force V2 detected by the voltmeter 104 is gradually decreased to 300 mV, 250 mV, and 220 mV respectively.

The degree of the decrease in electromotive force V2 represents the NO concentration. Namely, the electromotive force V2, which is outputted from the measuring oxygen partial pressure-detecting cell 100 constructed by the detecting electrode 102, the reference electrode 74, and the first solid electrolyte layer 52d, represents the NO concentration in the measurement gas.

In the oxide sensor 50D according to the fourth embodiment, the width w of the measuring electrode 72 along the downstream direction of the controlling oxygen partial pressure-detecting cell is also restricted to be in a range of $w \leq 5t$ provided that the height of the first chamber 60 is represented by t, in the same manner as the oxide sensor 50A according to the first embodiment. Further, the measuring electrode 72 is arranged at the position at which the projective distance d from the downstream end of the inner pumping electrode 64 (the end located on the side of the second diffusion rate-determining section 58) to the center of the measuring electrode 72 satisfies at least $-3t \leq d$. Preferably, the measuring electrode 72 is arranged to satisfy $-3t \leq d \leq 3t$.

Now, an illustrative experiment will be described. The illustrative experiment was carried out, as concerning designed Example and Comparative Example, in order to observe the change in electromotive force V2 of the oxygen concentration cell, generated between the detecting electrode 102 and the reference electrode 74 of the measuring oxygen partial pressure-detecting cell 100, obtained by changing the concentration of $O_2$ contained in a measurement objective gas (NO concentration=300 ppm), while adjusting the voltage V1 at 300 mV as the electromotive force of the oxygen concentration cell including the measuring electrode 72 for the first chamber 60. Results of the experiment are shown in FIG. 10.

The result concerning Example was obtained by using a relative arrangement of d=t for the measuring electrode 72 in the oxide sensor 50D according to the fourth embodiment. The result concerning Comparative Example was obtained by using a relative arrangement of d=−8t for the measuring electrode 72 in the oxide sensor 50D according to the fourth embodiment.

In Comparative Example based on the relative arrangement of d=−8t, the measuring point for the partial pressure of oxygen in the controlling oxygen partial pressure-detecting cell 76 is located at a position corresponding to an intermediate portion of the inner pumping electrode 64. Accordingly, when the concentration of $O_2$ contained in the measurement gas is increased, the control is performed so that the partial pressure of oxygen at the position at which the measuring electrode 72 is arranged becomes a target partial pressure of oxygen. In this case, the partial pressure of oxygen is further lowered by a residual portion of the inner pumping electrode 64 located downstream from the position at which the measuring electrode 72 is arranged. Therefore, the measurement gas is supplied to the second chamber 62 in a state in which the partial pressure of oxygen is lower than the target partial pressure of oxygen.

Figure 10:
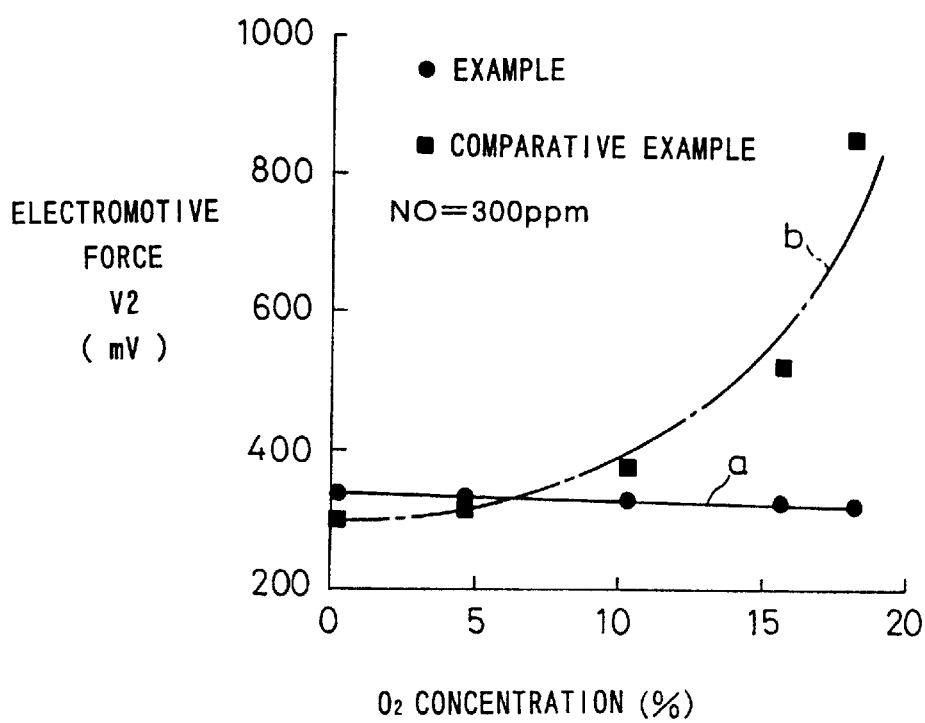
FIG. 10 shows characteristics of the oxide sensor according to the fourth embodiment, illustrating the change in electromotive force generated in the measuring oxygen partial pressure-detecting cell, obtained by changing the concentration of $O_2$ contained in a measurement gas (NO concentration=300 ppm) in a range of 0 to 18%, wherein a solid line represents a characteristic obtained in Example, and a chain line represents a characteristic obtained in Comparative Example.
Figure 11:
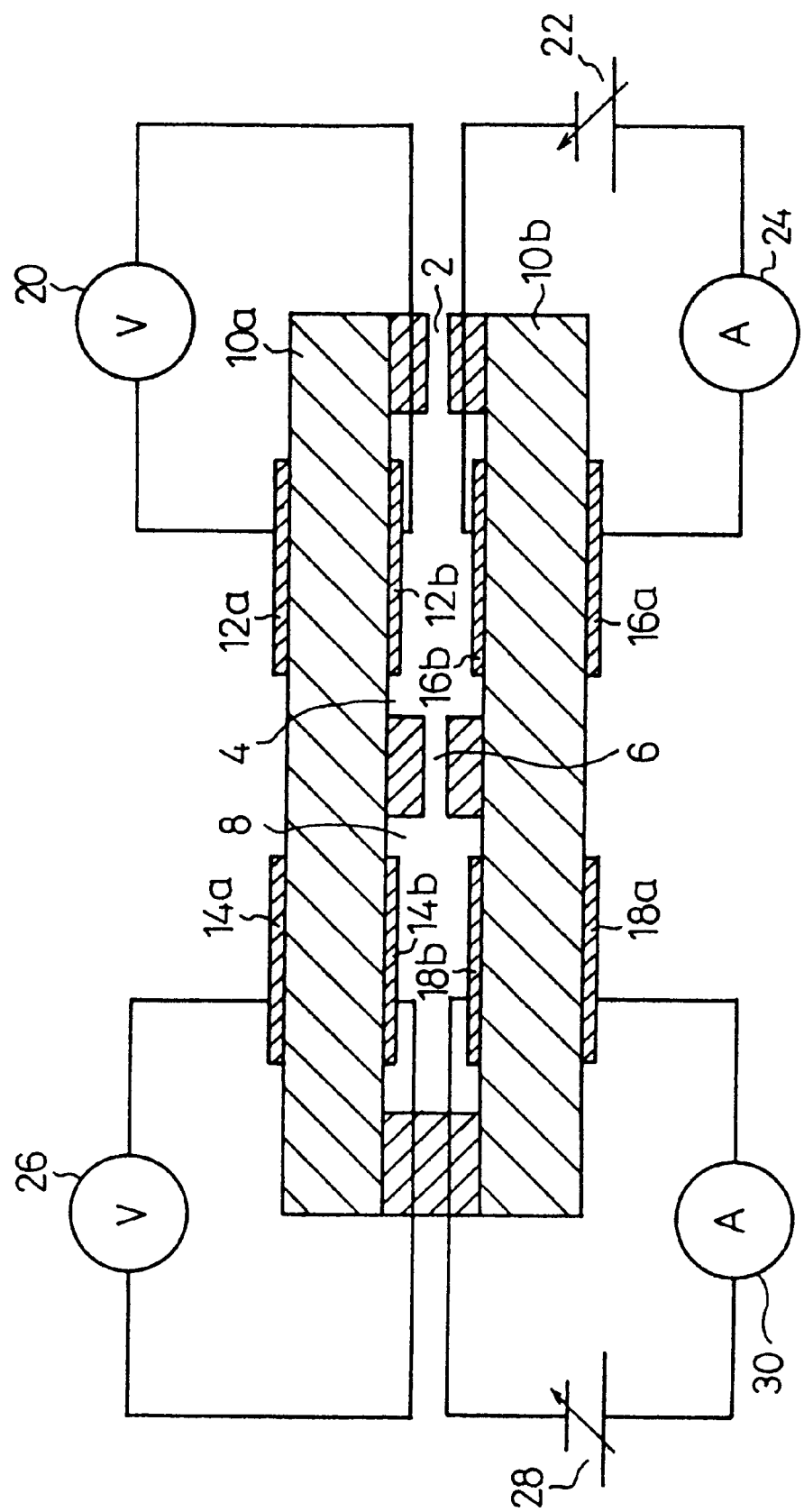
FIG. 11 shows a cross-sectional view illustrating a system of a gas analyzer concerning the conventional technique.

For this reason, in Comparative Example, when the concentration of $O_2$ contained in the measurement gas is increased, the electromotive force V2 of the oxygen concentration cell between the detecting electrode 102 and the reference electrode 74 of the controlling oxygen partial pressure-detecting cell 76 is increased in a manner of exponential function, as illustrated by a chain line b shown in FIG. 10.

On the contrary, in Example based on the relative arrangement of d=t, the measuring point for the partial pressure of oxygen in the controlling oxygen partial pressure-detecting cell 76 is located in the vicinity of the downstream end of the inner pumping electrode 64. Accordingly, the partial pressure of oxygen in the first chamber 60 is controlled to achieve a target partial pressure of oxygen at a position approximately corresponding to the downstream end of the inner pumping electrode 64. In this case, as illustrated by a solid line a shown in FIG. 10, the measurement gas adjusted to have the target partial pressure of oxygen by the aid of the main pumping cell 68 is supplied to the second chamber 62, in a state in which the target partial pressure of oxygen is substantially maintained.

As described above, as for the oxide sensor 50D according to the fourth embodiment, the objective components in the measurement gas can be supplied to the second chamber 62 without causing any decomposition, while allowing the measurement gas to have an optimum partial pressure of oxygen. Thus the oxides can be measured with a high degree of accuracy by the aid of the measuring oxygen partial pressure-detecting cell 100.

The oxide sensors 50A to 50D according to the first to fourth embodiments have been explained above, in which only one second chamber 62 is connected to the first chamber 60. However, the oxide sensor of the present invention may be constructed such that a plurality of second chambers 62 are connected to the first chamber 60 to simultaneously measure a plurality of oxides of different types.

It is assumed, for example, a third chamber constructed in the same manner as the second chamber 62 is connected in series to the second chamber 62 through a diffusion rate-determining section, and the measuring pumping cell is provided for the second chamber 62. A pumping voltage, which is different from the pumping electrode Vp2 applied to the detecting electrode 82 for the second chamber 62, is applied to a detecting electrode for the third chamber. Thus it is possible to measure an oxide which is different in type from that measured in the second chamber 62. Measurement can be performed in the same manner when the second chamber is provided with the measuring oxygen partial pressure-detecting cell in place of the measuring pumping cell.

The oxides to be measured in the second and third chambers include, for example, NO, $NO_2$, $CO_2$, $H_2O$, and $SO_2$. Alternatively, the third chamber may be connected in parallel to the second chamber 76.

It is a matter of course that the oxide sensor according to this invention is not limited to the embodiments described above, which can be constructed in other various forms without deviating from the gist or essential characteristics of this invention.

What is claimed is:

1. An oxide sensor comprising:
   a main pumping means including a first solid electrolyte for contacting with external space, and inner and outer electrodes formed on inner and outer surfaces of the first solid electrolyte, for performing a pumping process for oxygen contained in a measurement gas introduced from said external space, on said basis of a control voltage applied between said electrodes;
   a concentration-measuring means including a second solid electrolyte, an inner measuring electrode formed on the second solid electrolyte on a side opposite to inner measuring electrode, for measuring an electromotive force of an oxygen concentration cell, generated corresponding to a difference in partial pressure between oxygen resulting from said pumping process performed by said main pumping means and oxygen contained in a gas existing on a side of said outer measuring electrode;
   a main pumping control means for adjusting a level of said control voltage so that said electromotive force of said oxygen concentration cell detected by said concentration-measuring means has a predetermined value; and
   an electric signal-generating conversion means including the second solid electrolyte and inner and outer detecting electrodes provide in contact with the second solid electrolyte, for providing, by conversion, an electric signal corresponding to an amount of oxygen contained in said measurement gas after being subjected to said pumping process performed by said main pumping means, wherein:
      said inner measuring electrode is arranged at a position at which $-3t \leq d$ is satisfied provided that a downstream direction along a space for said pumping process performed by said main pumping means is defined as a positive direction, a height of said space for said pumping process is represented by t, and a protective distance between a downstream end of said inner pumping electrode of said main pumping means and a center of said inner measuring electrode of said concentration-measuring means is represented by d, and wherein:
         oxides in said measurement gas are measured on the basis of said electric signal supplied from said electric signal-generating conversion means.

2. The oxide sensor according to claim 1, wherein said electric signal-generating conversion means further comprises:
   a measuring pumping means including the second solid electrolyte, said inner detecting electrode formed on the second solid electrolyte on a side opposite to said inner detecting electrode, for performing a pumping process for said oxygen contained in said measurement gas after being subjected to said pumping process performed by said main pumping means, on the basis of a measuring voltage applied between said inner and outer detecting electrodes; and
   a current-detecting means for detecting a pumping current generated corresponding to an amount of said oxygen subjected to said pumping process performed by said measured pumping means, wherein:
      said oxides in said measurement gas are measured on the basis of said pumping current detected by said current-detecting means.

3. The oxide sensor according to claim 2, wherein said measuring pumping means performs said pumping process for said oxygen produced by any one of or both of actions of application of a voltage sufficient to decompose said oxides between said inner and outer detecting electrodes, and an oxide-decomposing catalyst arranged in said measuring pumping means, on the basis of said measuring voltage applied between said inner and outer detecting electrodes.

4. The oxide sensor according to claim 3, wherein said oxide-decomposing catalyst is an Rh cermet.

5. The oxide sensor according to claim 1, wherein, said electric signal-generating conversion means further comprises:
   a concentration-detecting means including the second solid electrolyte, an inner detecting electrode formed on the second solid electrolyte, and said outer electrode formed on the second solid electrolyte on a side opposite to said inner detecting electrode, for generating an electromotive force corresponding to a difference between an amount of oxygen contained in said measurement gas after being subjected to said pumping process performed by said main pumping means and an amount of oxygen contained in said gas existing on said side of said outer detecting electrode; and
   a voltage-detecting means for detecting said electromotive force generated by said concentration-detecting means, wherein:
      said oxides in said measurement gas are measured on the basis of said electromotive force detected by said voltage-detecting means.

6. The oxide sensor according to claim 5, wherein said concentration-detecting means generates said electromotive force of an oxygen concentration cell, corresponding to a difference in partial pressure between oxygen produced by an action of an oxide-decomposing catalyst arranged in said concentration-detecting means and said oxygen contained in said gas existing on said side of said outer detecting electrode.

7. The oxide sensor according to claim 6, wherein said oxide-decomposing catalyst is an Rh cermet.

8. The oxide sensor according to claim 1, wherein said inner measuring electrode of said concentration-detecting means is arranged at a position at which $-3t \leq d \leq 3t$ is satisfied.

9. The oxide sensor according to claim 1, wherein said inner measuring electrode of said concentration-measuring means has a width w along said downstream direction which satisfies $w \leq 5t$.

10. The oxide sensor according to claim 1, wherein said inner pumping electrode of said main pumping means is composed of an inactive material having a low catalytic activity on said oxides.

11. The oxide sensor according to claim 1, wherein said oxides are nitrogen oxides.

12. The oxide sensor according to claim 1, further comprising an auxiliary pumping means including an auxiliary pumping electrode formed in the vicinity of said inner detecting electrode, wherein said oxygen contained in said measurement gas after being subjected to said pumping process performed by said main pumping means is subjected to a pumping process on the basis of a voltage applied between said auxiliary pumping electrode and said outer detecting electrode.

13. The oxide sensor according to claim 1, wherein said outer measuring electrode is arranged at a position exposed to a space into which a reference gas is introduced.

14. The oxide sensor according to claim 1, wherein said outer measuring electrode and said outer detecting electrode are combined into a common unit.

15. The oxide sensor according to claim 1, wherein:

said main pumping means includes said inner and outer pumping electrodes formed at the inside and the outside of a first chamber surrounded by solid electrolyte substrates, for introducing said measurement gas thereinto, and said substrate interposed between said both electrodes;

said concentration-measuring means includes said measuring electrode formed at the inside of said first chamber, a reference electrode formed in a reference gas-introducing space surrounded by said solid electrolyte substrates, for introducing a reference gas thereinto, and said substrate interposed between said measuring electrode and said reference electrode; and said electric signal-generating conversion means includes said detecting electrode formed at the inside of a second chamber surrounded by said solid electrolyte substrates, for introducing said measurement gas thereinto after being subjected to said pumping process performed by said main pumping means, a reference electrode formed at the inside of said reference gas-introducing space, and said substrate interposed between said detecting electrode and said reference electrode.

16. The oxide sensor according to claim 15, further comprising:

a first diffusion rate-determining section for giving a predetermined diffusion resistance to said measurement gas, provided at a passage for introducing said measurement gas from said external space into said first chamber; and a second diffusion rate-determining section for giving a predetermined diffusion resistance to said measurement gas, provided at a passage for introducing said measurement gas into said second chamber after being subjected to said pumping process performed by said main pumping means.

17. The oxide sensor according to claim 15, wherein said inner pumping electrode and said measuring electrode are arranged on an identical plane of any one of said substrates in said first chamber.

18. The oxide sensor according to claim 15, further comprising:

a plurality of diffusion rate-determining sections for giving predetermined diffusion resistances to said measurement gas supplied from said first chamber; and a plurality of second chambers as defined above for measuring said oxides of different types respectively.

19. The oxide sensor according to claim 18, wherein said plurality of second chambers are arranged in series to said first chamber.

20. The oxide sensor according to claim 18, wherein said plurality of second chambers are arranged in parallel to said first chamber.

21. The oxide sensor according to claim 15, further comprising a third diffusion rate-determining section for giving a predetermined diffusion resistance to said measurement gas, provided at a passage for allowing said measurement gas in said second chamber to approach said detecting electrode.

* * * * *